United States Patent [19]
Eden et al.

[11] Patent Number: 5,207,293
[45] Date of Patent: * May 4, 1993

[54] METHOD AND APPARATUS FOR LUBRICATING STOPPERS FOR SYRINGE BARRELS

[75] Inventors: Robert Eden, Holdrege; Roger Hoeck, Loomis; Merlyn Urbom, Holdrege, all of Nebr.

[73] Assignee: Becton, Dickinson and Company, Franklin Lakes, N.J.

[*] Notice: The portion of the term of this patent subsequent to Oct. 27, 2009 has been disclaimed.

[21] Appl. No.: 902,610

[22] Filed: Jun. 23, 1992

Related U.S. Application Data

[63] Continuation of Ser. No. 406,622, Sep. 13, 1989, Pat. No. 5,158,154.

[51] Int. Cl.$^5$ .............................................. F16N 25/04
[52] U.S. Cl. ...................................... 184/101; 184/17; 29/458; 29/527.2
[58] Field of Search ............... 29/458, 527.2; 604/230; 184/15.1, 17, 101, 109

[56] References Cited

U.S. PATENT DOCUMENTS

| | | | |
|---|---|---|---|
| 945,622 | 1/1910 | Slaughter | 184/17 |
| 1,140,475 | 5/1915 | Mulholland | 184/17 |
| 2,764,126 | 9/1956 | Thomas | 118/612 |
| 3,195,681 | 7/1965 | Hirata | 184/3 |
| 3,633,322 | 1/1972 | Morcom | 51/323 |
| 3,958,570 | 5/1976 | Vogelman et al. | 128/218 |
| 4,172,155 | 10/1979 | Pease | 427/34 |
| 4,767,414 | 8/1988 | Williams et al. | 604/230 |
| 4,901,820 | 2/1990 | Fry et al. | 184/64 |
| 5,158,154 | 10/1992 | Eden et al. | 184/101 |

Primary Examiner—Ira S. Lazarus
Assistant Examiner—Alan B. Cariaso
Attorney, Agent, or Firm—Nanette S. Thomas

[57] ABSTRACT

A method and apparatus for lubricating stoppers prior to their insertion with syringe barrels is provided. A pair of lubricating wheels are provided which have opposing stopper contact surfaces. Each wheel is partially positioned within a reservoir so that, upon wheel rotation, lubricant within the reservoir is transferred to a wheel engaging the stopper contact surfaces.

16 Claims, 3 Drawing Sheets

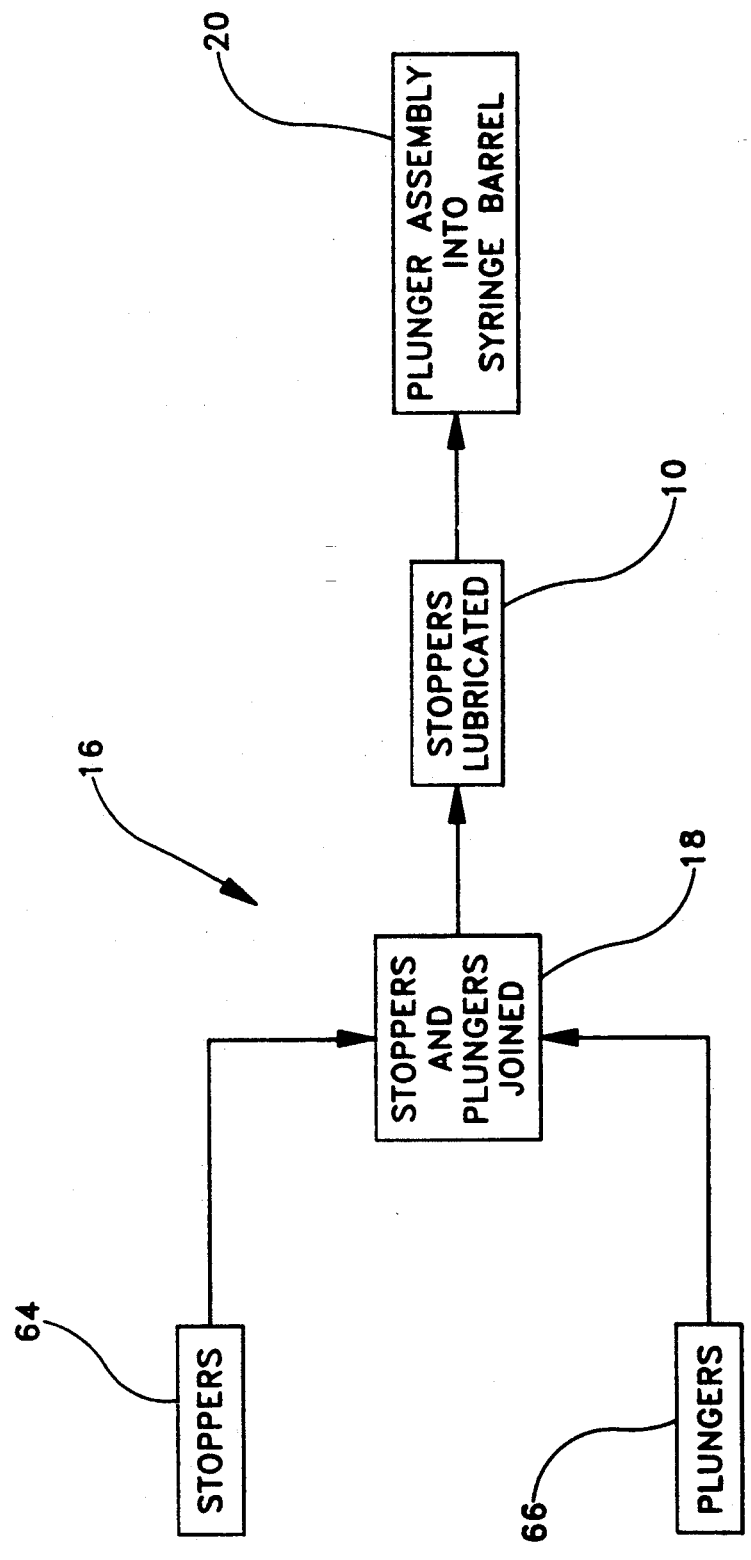

METHOD AND APPARATUS FOR LUBRICATING STOPPERS FOR SYRINGE BARRELS

This is a continuation of co-pending application Ser. No. 07/406,622 filed Sep. 13, 1989, now U.S. Pat. No. 5,159,154.

BACKGROUND OF THE INVENTION

The field of the invention relates to methods and apparatus for assembling syringes and other such medical devices which include a stopper and plunger assembly for drawing or ejecting fluids.

Syringes are generally comprised of a cylindrical barrel, a cannula secured to one end of the barrel, a stopper within the barrel, and a plunger secured to the stopper for moving it within the barrel. The barrel, plunger and stopper are often molded from various thermoplastic materials. The cannula is usually made from metal such as stainless steel.

The manufacture of syringes typically involves the use of a machine for assembling the barrel/cannula assembly with the other molded components. Barrel/cannula assemblies, complete with shields for protecting the cannulas, are loaded into the machine while plungers and stoppers are loaded into separate machine feed hoppers. The stoppers flow to a feed bowl or the like from where they are fed to a track and then to a dial. A dial is a disk shaped metal (or non-metal) article having slots for retaining selected items. In the meantime, the plungers move along a track to another dial adjacent to the stopper dial but at a different height within the machine. The plungers and stopper held by the respective dials are moved into engagement with each other and joined. This subassembly is then transferred to another dial from where it is inserted within the syringe barrel.

It is important to provide lubrication between the stopper and the inner wall of the syringe barrel so that the syringe can be operated smoothly. A medical grade of silicone oil or lubricant has typically been applied directly to the inner walls of the syringe barrel prior to insertion of the plunger/stopper subassembly. This technique has several drawbacks, however. One is the risk of placing more silicone oil into the barrel than is necessary for the proper functioning of the syringe assembly. This may alter test results on fluids, such as blood, collected within the syringe or possibly compromise drug therapy. In addition to slowing down the assembly process, there is also the risk of excess oil falling on parts of the assembly machine, thereby necessitating more frequent cleaning.

SUMMARY OF THE INVENTION

It is an object of the invention to provide an apparatus for lubricating stoppers prior to their insertion within a syringe barrel.

It is another object of the invention to control the amount of lubricant inserted within a syringe barrel while insuring smooth operation of the syringe.

In accordance with these and other objects of the invention, an apparatus is provided including a lubricating wheel, means for rotating said lubricating wheel, and means for moving a stopper adjacent to said wheel such that said stopper is contacted by said wheel.

In addition, a method for assembling a syringe is provided which comprises the steps of providing a plunger having a stopper secured to one end thereof, applying a lubricant to said stopper, and inserting said stopper and at least part of said plunger within a syringe barrel.

The method and apparatus according to the invention allow a syringe to be assembled at high speed while reducing the possibility of excess oil being present within syringe barrels or otherwise contaminating parts of the assembly machine.

BRIEF DESCRIPTION OF THE DRAWINGS

FIG. 4 is a schematic illustration of the major functional components of a syringe assembly machine according to the invention.

DETAILED DESCRIPTION OF THE INVENTION

Figure 1:
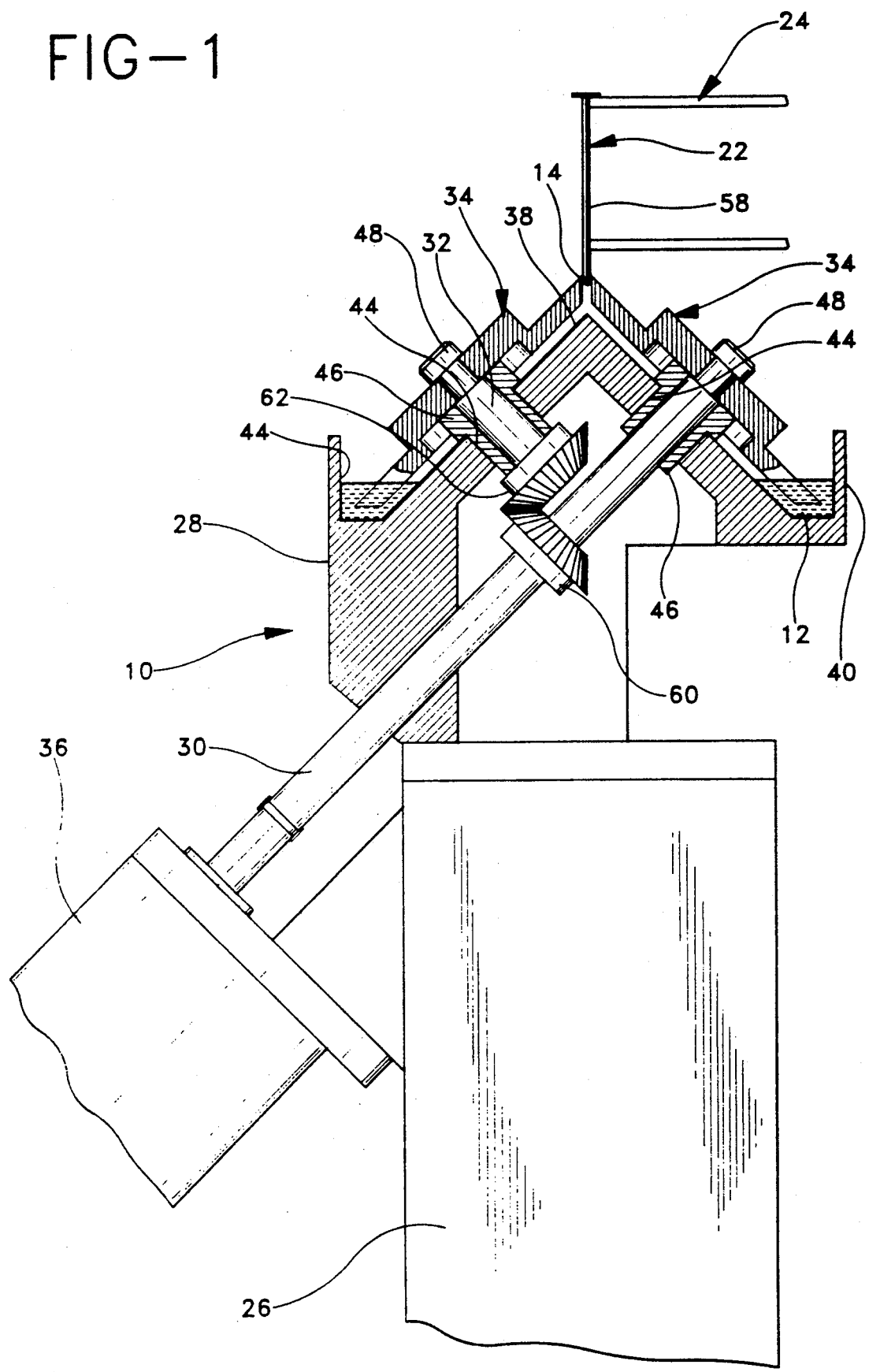
FIG. 1 is a partially sectioned side elevation view of an apparatus for lubricating stoppers within a syringe assembly machine.

A lubricating apparatus 10 for applying a lubricant such as silicone oil 12 to a stopper 14 is shown in FIG. 1. The apparatus is contained within a machine 16 for assembling syringes from prefabricated components, the machine being diagrammatically illustrated in FIG. 4. The apparatus 10 is positioned after the assembly equipment 18 which joins the stoppers to plungers, but before the assembly equipment 20 which inserts the plunger/stopper subassemblies 22 into syringe barrels.

As shown in FIG. 1, a plunger/stopper subassembly 22 is transported in the vertical position to the apparatus by a dial 24. The stopper end faces downwardly when positioned within the apparatus 10.

The apparatus 10 is mounted to a support 26 within the assembly machine 16. It includes a body portion 28, a main shaft 30, a short shaft 32, and a pair of lubricating wheels 34 mounted to the respective shafts. A gearmotor 36 is provided for driving the two shafts at the same rotational velocity when the wheels, such as in this embodiment, are of the same diameter.

The body portion 28 includes a conical top portion 38 and an annular rim 40. An annular reservoir 42 is defined between the conical top portion 38 and the rim 40. The silicone oil 12 is retained by the reservoir.

A pair of circular openings 44 are provided within the conical top portion 38 of the body portion 28. The axes of these openings run perpendicularly to each other. A bushing 46 is provided within each opening. The main shaft 30 passes through one of these bushings 46 while the short shaft 32 extends through the other of the two bushings.

One of the lubricating wheels 34 is mounted to the main shaft 30 while the other is mounted to the short shaft. They are secured to the respective shafts by a pair of pins 48. Each is spaced from the outer surface of the conical top portion 38 of the body portion 28 by a rim protruding from each bushing 46. The wheels 34 are oriented at right angles to each other.

Figure 2:
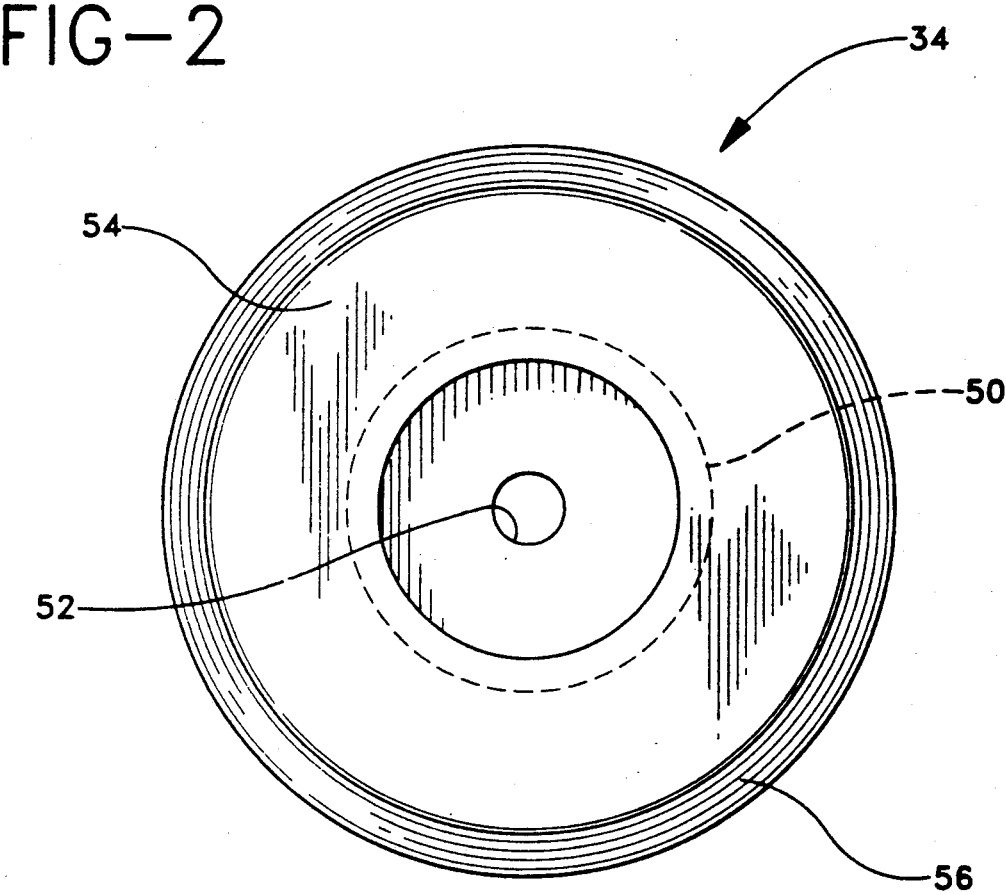
FIG. 2 is a bottom plan view of a lubricating wheel as shown in FIG. 1.
Figure 3:
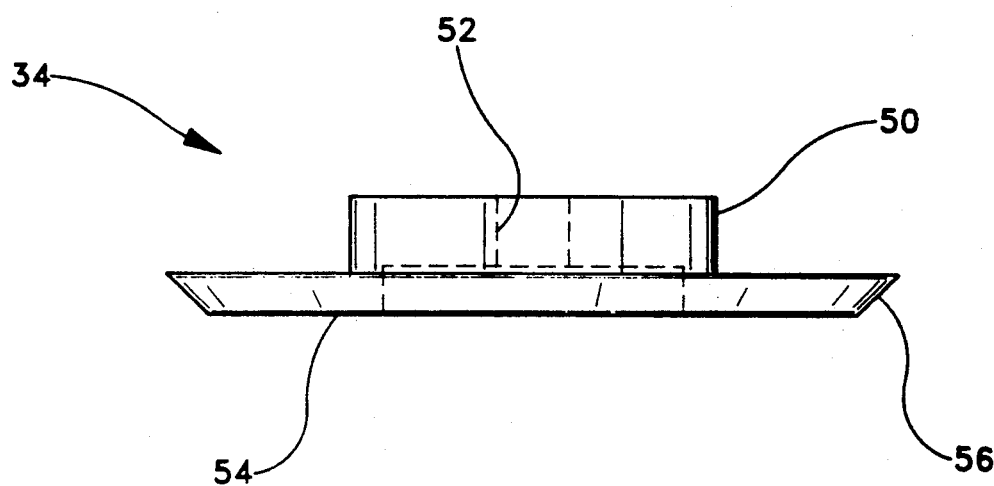
FIG. 3 is a side elevation view thereof.

Referring to FIGS. 2 and 3, each lubricating wheel 34 includes a cylindrical body portion 50 preferably made from stainless steel and having a central opening 52 extending therethrough. A rim 54 having a bevelled lower surface 56 extends from the cylindrical body portion 50. The diameter of the wheel is about four inches in this embodiment. This size wheel may be used for lubricating a stopper having a diameter of about 0.13 inches and a length of about 0.2 inches. Stoppers of this size are used within relatively small syringes, such as 0.3 cc syringes. It will be appreciated that the dimensions of the wheels and the other components of the apparatus may be substantially different. Wheels of larger diameter, such as about eighteen inches, are likely to be preferable as they do not need to be rotated at as high a rotational speed as those of smaller diameter.

Each lubricating wheel is mounted such that a portion of its rim extends within the reservoir 42. Doctor blades (not shown) control the amounts of lubricant carried by the wheels. The portions of the respective rims of each wheel 180° from the reservoir are in opposing relation to each other and are separated by a distance corresponding to about the diameter of a stopper 14. Each bevelled surface 56 in this embodiment is cut at about a 45° angle with respect to the wheel so as to make flush contact with the stopper 14 secured to each plunger 58 as it is passed between the wheels by the dial 24.

The lower surface 56 of each lubricating wheel 34 may be mechanically engraved with a fine cell structure to facilitate and meter the transfer of oil from the reservoir. Wheels or rolls including such engravings are referred to as anilox rolls in the printing industry. Doctor blades (not shown) are preferably used in conjunction therewith to control the amount of oil which is carried by the wheels to the stoppers.

A first gear 60 is mounted to the main shaft 30 within the body portion 28 of the apparatus 10. A second gear 62 is mounted to the short shaft 32 and engages the first gear Rotation of the main shaft 30 by the gearmotor 36 accordingly causes the short shaft to rotate at the same speed.

In operation, prefabricated stoppers 14 and plungers 58 are loaded into the assembly machine 16 and directed to separate feed bowls 64, 66. The stoppers and plungers are transferred by dials (not shown) to the plunger/stopper assembly equipment 18 where they are joined. An assembly machine dial 24 picks up the plunger/stopper subassemblies 22 and transports them to the lubricating apparatus 10.

The lubricating wheels 34 of the lubricating apparatus 10 are continuously rotated at a speed of about 160 rpm when four inch wheels are employed, thereby coating the bevelled lower surfaces 56 thereof with a lubricant such as medical grade silicone oil 12 from the reservoir 42. The viscosity of the medical grade lubricant should be chosen for proper syringe performance and compatibility with the manufacturing process. Medical grade silicone lubricant having a viscosity of 12,500 centistokes is desirable. The dial 24 moves each subassembly 22 so that each stopper 14 is positioned between and in contact with the wheels 34 as shown in FIG. 1. Silicone oil is thereby transferred by the rotating wheels to the stoppers as they pass through the lubricating apparatus 10. Excess oil simply works its way back down to the reservoir via the wheels or the upper surface of the conical top portion 38 of the apparatus.

Each subassembly 22 is subsequently transported to assembly equipment 20 which inserts it within a syringe barrel (not shown). The stopper 14, which is coated with oil, lubricates the walls of the syringe barrel upon insertion. Means (not shown) may be provided for exercising the plunger/stopper subassemblies 22 within the syringe barrels to insure smooth operation when they are ultimately used in the field.

In the above described manner, the lubricating apparatus 10 allows the high speed lubrication of the stopper and syringe barrel of a syringe. The possibility of excess oil being injected into a syringe barrel is substantially eliminated. The apparatus 10 is readily incorporated as part of conventional syringe assembly machines, and does not interfere with the standard assembly process. In fact, the cost of the syringe assembly machine is reduced by using the lubricating apparatus in accordance with the instant invention in place of the injection nozzle assemblies which have been conventionally employed.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An apparatus for lubricating stoppers for use within syringe barrels, comprising:
   a first lubricating wheel comprising a stopper contact surface which is defined by an annular edge;
   means for applying a lubricant to said first lubricating wheel;
   means for rotating said first lubricating wheel; and
   means for moving said stopper into contact with said stopper contact surface of said first lubricating wheel.

2. An apparatus as defined in claim 1 wherein said moving means includes means for moving a plunger/stopper subassembly towards said annular edge of said lubricating wheel.

3. An apparatus as defined in claim 1 further comprising a second lubricating wheel, including a stopper contact surface defined by an annular edge and which is partially in opposing relation to said stopper contact surface of said first lubricating wheel.

4. An apparatus as defined in claim 3 including a body portion which defines a reservoir, a shaft extending through said body portion, said first lubricating wheel being mounted to said shaft, a portion of said first lubricating wheel being positioned within said reservoir.

5. An apparatus as defined in claim 4 wherein said body portion includes an inclined upper surface adjoining said reservoir.

6. An apparatus as defined in claim 4 including means for rotating said shaft.

7. An apparatus as defined in claim 4 wherein said moving means includes means for moving a plunger/stopper assembly towards said first lubricating wheel.

8. An apparatus as defined in claim 7 wherein said moving means includes means for moving said stopper between said opposing portions of said stopper contact surfaces.

9. An apparatus as defined in claim 1 including a reservoir, a portion of said first lubricating wheel being positioned within said reservoir.

10. An apparatus as defined in claim 3 including means for rotating each of said lubricating wheels at the same speed.

11. In a syringe assembly machine including means for joining stoppers and plungers and means for inserting plunger/stopper assemblies into respective syringe barrels, the improvement comprising means for applying a lubricant to said stoppers of said stopper/plunger assemblies prior to inserting said plunger/stopper assemblies into said respective syringe barrels wherein said means for applying a lubricant to said stopper comprises:

a first lubricating wheel including a stopper contact surface defined by an annular edge;

means for applying a lubricant to said first lubricating wheel;

means for moving a plunger/stopper assembly towards said first lubricating wheel so that the stopper of said plunger/stopper assembly contacts said stopper contact surface of said first lubricating wheel; and means for rotating said first lubricating wheel.

12. The syringe assembly machine of claim 11 further comprising a second lubricating wheel, including a stopper contact surface defined by an annular edge, a portion of said stopper contact surface of said second lubricating wheel being in opposing relation to a portion of said stopper contact surface of said first lubricating wheel.

13. The improvement of claim 12 including a body portion which defines a reservoir, a shaft extending through said body portion, said first lubricating wheel being mounted to said shaft, a portion of said first lubricating wheel being positioned within said reservoir.

14. The improvement of claim 12 including a reservoir, a portion of said first lubricating wheel being positioned within said reservoir.

15. The improvement of claim 9 including means for rotating each of said lubricating wheels at the same speed.

16. The improvement of claim 12 wherein said moving means includes means for moving a plunger/stopper assembly in a vertical position between said opposing stopper contact surfaces of said lubricating wheels.

* * * * *